US 6,616,914 B2

(12) United States Patent
Ward et al.

(10) Patent No.: US 6,616,914 B2
(45) Date of Patent: Sep. 9, 2003

(54) METHOD FOR PULMONARY AND ORAL DELIVERY OF PHARMACEUTICALS

(75) Inventors: Gary Ward, San Diego, CA (US); Robert Schultz, San Diego, CA (US)

(73) Assignee: Elan Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/907,393

(22) Filed: Jul. 17, 2001

(65) Prior Publication Data

US 2001/0041190 A1 Nov. 15, 2001

Related U.S. Application Data

(62) Division of application No. 09/480,549, filed on Jan. 10, 2000.

(51) Int. Cl.$^7$ .............................. A61K 9/12; A61K 9/14; A61K 9/72; A61K 38/28
(52) U.S. Cl. .................. 424/45; 424/46; 424/489; 424/499; 514/2; 514/3; 514/866; 128/200.14; 128/203.15
(58) Field of Search .................. 424/45, 46, 489, 424/499; 514/2, 3; 128/200.14, 203.15, 866

(56) References Cited

U.S. PATENT DOCUMENTS

| 5,260,306 A | 11/1993 | Boardman et al. |
|---|---|---|
| 5,518,998 A | 5/1996 | Bäckström et al. |
| 5,874,064 A | 2/1999 | Edwards et al. |
| 6,167,880 B1 * | 1/2001 | Gonda et al. .......... 128/200.14 |
| 2001/0006939 A1 * | 7/2001 | Niven et al. .................... 514/2 |

FOREIGN PATENT DOCUMENTS

| WO | WO 0066206 | * | 9/2000 |
|---|---|---|---|

OTHER PUBLICATIONS

Drug Information Handbook, 1993, Lexi–corp, Lacy et al.*

* cited by examiner

Primary Examiner—Michael G. Hartley
Assistant Examiner—M. Haghighatian
(74) Attorney, Agent, or Firm—Perkins Coie LLP

(57) ABSTRACT

In a powder formulation for use in a dry powder inhaler, a pharmaceutical acts as its own carrier, so that use of lactose or other excipients are not needed. The dry powder formulation has a single active pharmaceutical compound having two major populations in particle size distribution: microfine particles of the active pharmaceutical, of 1–10 microns in diameter, and larger carrier particles, also of the active pharmaceutical compound. The carrier particles provide a long acting, delayed onset, and optionally therapeutic effect via the GI tract, while the microfine particles provide a fast onset effect via the lung.

23 Claims, No Drawings

METHOD FOR PULMONARY AND ORAL DELIVERY OF PHARMACEUTICALS

This is a divisional of U.S. patent application Ser. No. 09/480,549, filed Jan. 10, 2000, now pending, and incorporated herein by reference.

BACKGROUND OF THE INVENTION

The field of the invention is inhalers and pharmaceutical formulations for use in inhalers.

Dry powder inhalers have been successfully used to deliver pharmaceuticals into the lungs, primarily for treatment of asthma and other pulmonary conditions. Use of an inhaler for delivery of a pharmaceutical is advantageous as it is relatively simple, fast, comfortable, and pain-free for the patient. Due to the nature of the absorption within the lungs, inhaled pharmaceuticals tend to be very fast acting. Inhalation usually provides a very fast rise of the level of the pharmaceutical in the blood, when compared to other delivery techniques, such as oral or transdermal delivery. For example, albuterol is a bronchodialator which acts rapidly when inhaled to treat an asthma attack, a condition for which treatment with a solid oral dosage form may be too slow. While this rapid absorption is often advantageous, it can also require relatively frequent dosing via inhalation, to provide a sustained effect. In contrast, oral delivery, which provides absorption of the drug via the gastrointestinal (GI) tract, generally provides a much more slowly acting, but also often a more sustained, therapeutic effect. For many pharmaceuticals, the delay in the onset of the therapeutic effect is a significant disadvantage.

Thus, each pharmaceutical delivery route (via the GI tract, and via inhalation into the lungs) has advantages and disadvantages, depending on the pharmaceutical used and the therapeutic effect desired. However, the advantages of each route have not, until now, been combined, to achieve the advantages of both routes, in a single dose or step.

Many patients must regularly take two or more pharmaceuticals. The pharmaceuticals may act independently to treat unrelated conditions, or they may act together, or complement each other, in treating a single condition. The dosing regimen for combinations of pharmaceuticals often require that they be taken at the same time. This may require taking 2 or more capsules or tablets from different bottles, a combination of such oral dose forms and a pharmaceutical delivered via another route, or some other combination of delivery routes. For example, patients with Type 2 diabetes will often be prescribed doses of insulin, via injection, along with a hypoglycemic drug in an oral dose form.

The need for separate dosing is less convenient for the patient than taking a single dose. The patient must: maintain a supply of both (or all) of the separate pharmaceuticals; remember to take each one; and go through the separate actions of taking each one. Accordingly, the dosing regimen is more complicated, and difficult to maintain (when compared to a single dosing regimen), especially for classes of patients having a disability due to sickness, injury, age, or medical condition.

For patients taking more than one pharmaceutical, complying with their prescribed dosing regimen can be less consistent, due to the need to separately take each of the pharmaceuticals. To achieve the full therapeutic effect of the prescribed pharmaceuticals, it is generally important to maintain consistent compliance. Thus any pharmaceutical delivery techniques which can improve patient compliance will help to improve the patients health. Consequently, for many patients, it would be highly advantageous to be able to combine separate dosing regimens into a single joint dosing regimen. Reducing multiple dosing regimens to a single dosing regimen improves the convenience to the patient, and makes compliance to the prescribed dosing regimen easier, and thus more likely to be consistently followed.

Accordingly, it is an object of the invention to provide a pharmaceutical formulation for use in an inhaler, which provides the rapid onset or effect of an inhaled pharmaceutical, along with the slower onset and/or the longer acting effect of a pharmaceutical delivered via the GI tract.

It is a further object of the invention to provide a pharmaceutical formulation for use in an inhaler which can combine multiple dosing regimens into a single action, to improve the convenience to the patient, and to improve patient compliance to the prescribed dosing regimen.

SUMMARY OF THE INVENTION

In a first aspect of the invention, a pharmaceutical formulation includes microfine active particles preferably of about 1–10 microns in diameter and carrier particles preferably of about 10–100 or larger, and preferably greater than 50 microns in diameter. The microfine particles and the carrier particles are both made of an active pharmaceutical compound. The carrier particles and the microfine particles may be the same active pharmaceutical compound, or they may be different active pharmaceutical compounds. At least some of the microfine particles may be attached to and carried by the larger carrier particles.

In a second aspect of the invention, upon inhalation, the microfine particles and carrier particles are separated, preferably through input of mechanical or electrical energy. The microfine particles travel through the throat and pass into the lungs. The carrier particles pass into the throat, and are swallowed. Accordingly, active pharmaceuticals are delivered to both the lungs (for a rapid onset or fast acting effect) and to the GI tract (for a slower onset or a more sustained effect). The swallowed dose is preferably at least 10 times greater in weight than the inhaled dose, and preferably is at least 50, 100, or even 1,000 times greater.

DETAILED DESCRIPTION OF THE INVENTION

In a first embodiment of the invention, a dry powder formulation for use in a dry powder inhaler has a pharmaceutical which acts as its own carrier. The formulation has a single active pharmaceutical component, formulated such that it has two major populations in the particle size distribution. The first population includes larger active carrier pharmaceutical particles, e.g., 10–2000 microns in diameter, preferably 30–300 microns in diameter, and most preferably 50–100 microns in diameter (average volume median diameter).

The second population includes microfine active pharmaceutical particles, of 1–10 microns in diameter, and preferably 1–5 microns in diameter.

At least some of the microfine particles attach themselves to the carrier particles, due to surface interactions, as is well known in the particle technology field. Consequently, in this embodiment, the active carrier particles carry the microfine particles, in much the same way as an excipient, such as e.g., lactose in conventional formulations. However, since the carrier particles also comprise an active pharmaceutical compound, the disadvantages of using lactose (interactions with the pharmaceutical and/or water vapor) are avoided, while aerosol performance is maintained. In addition, the delayed onset and/or sustained therapeutic benefits of delivery of the active carrier particles to the GI tract, are obtained.

The single component formulation described above can be used in the same way as conventional microfine active pharmaceutical/lactose or other excipient formulations. However, with convention formulations, after inhalation, the lactose serves no purpose. The lactose or excipient particles, generally exceeding the particle size range for inhalable particles (e.g., 1–10 microns), impact the mouth or throat, and are then swallowed, with no added therapeutic result.

The onset of the therapeutic effect provided by these carrier particles will be delayed relative to the therapeutic effect provided by the microfine particles, with all or almost all drugs. The duration of the therapeutic effect provided by the carrier particles may be comparable to, or greater than the duration of the therapeutic effect provided by the microfine particles. The delayed onset extends the total combined duration of the inhaled/swallowed dose. The carrier particles may also be prepared (e.g., coated) so that they provide a sustained, long duration therapeutic effect.

In contrast, with the single component formulation of the invention, as described above, the carrier particles, which impact the mouth or throat, and are swallowed, are active drug particles, which add a therapeutic effect, via absorption by the GI tract. If the specific pharmaceutical used in the single component formulation is not absorbable, then the active pharmaceutical carrier particles will not provide any added therapeutic effect via the GI tract. However, the disadvantages of including a sugar excipient, e.g. lactose, are still avoided. On the other hand, if the specific pharmaceutical is absorbable via the GI tract, then the additional therapeutic effect through the GI tract is achieved.

In prior known formulations used with inhalers, some active drug particles may be deposited in the throat and swallowed. However, the amount swallowed does not, and is not intended to, provide a therapeutic effect. These known formulations, used with existing inhalers, such as the Rotohaler® dry powder inhaler, generally have not delivered sufficient dry powder into the GI tract to provide a therapeutic effect. Indeed, their objective is to deliver all of the powder into the lungs. The powder delivered to the GI tract has been delivered to the throat only due to inefficiencies in the inhaler technology and formulations.

In the present formulation, generally the dose delivered to the GI tract will be much greater, e.g. 10–50, 10–100, or 10–1,000 times greater (by weight) than the dose delivered to the lungs. For example, with albuterol, the oral dose may be 10 milligrams, whereas the dose to the lungs may be 100 micrograms. The dose to the lungs provides a rapid onset (i.e., within 30 minutes, and preferably within 15, 10, or even 5 minutes) therapeutic effect. The dose to the GI tract provides a delayed or slower onset, i.e., providing a therapeutic effect which typically begins to occur in greater than 30 minutes.

The combined delivery to both the lung and the GI tract is especially useful for drugs or pharmaceutical compounds where both fast and slower and/or sustained action is beneficial, for example, with pain relief drugs. With the single component formulation described above, very fast therapeutic action is obtained from the absorption of the microfine particles passing into the lung. In addition, slower onset, optionally with longer term therapeutic effects, are obtained from the active pharmaceutical carrier particles deposited in the mouth or throat, swallowed, and then absorbed via the GI tract. The carrier particles may be coated to provide improved sustained release. Thus the present formulation provides a therapeutic effect which is faster than oral delivery alone. It may also provide, with some pharmaceuticals, a therapeutic effect which is longer acting than conventional inhaled formulations.

In a two component embodiment of the invention, the carrier particles and microfine particles are different active pharmaceutical compounds. Specifically, the pharmaceutical compound of the carrier particles is selected to provide for absorption via the GI tract, while the pharmaceutical compound for the microfine particles is a different pharmaceutical compound intended for delivery to the lung. An example of a 2 component embodiment is insulin as the microfine particles, and oral hypoglycemics or mimetics as the carrier particles. Multiple component formulations, having several active pharmaceutical microfine particles and carrier particles, may also be used. In another embodiment, the microfine particles may be substantially separated (not attached to) the carrier particles.

The formulations described above are useful with a wide range of drugs including beta-agonists such as albuterol; anti-inflammatories; analgesics; narcotics; anti-hypertensives; drugs for treating: motion sickness, pain, cancer, COPD, antiemetics, and others. The formulations of the invention contemplate use of potent drugs as the microfine component, consistent with the delivery of small doses to the lung. Inhaled doses generally cannot exceed 50 mg in a single dose, without causing the patient to cough. Hence, the microfine particle component should range from a few micrograms up to 50 mg in a single inhaled dose. The microfine particles are also preferably not irritating to the lung. On the other hand, the oral component, i.e., the carrier particles, can comprise a much larger dose. The carrier particles are also preferably compatible with GI tract delivery.

The present formulation is preferably delivered using a high efficiency inhaler, such as described in U.S. Pat. Nos. 5,577,497; 5,622,166; and WO 98/03217, incorporated herein by reference. Preferably, at least 20%, and more preferably, at least 30% or even 40% of the microfine component of the dose emitted from the inhaler is respirable.

Thus, a novel dry powder formulation and inhalation method have been described. Various changes and uses of substitutes may of course be made, without departing from the spirit and scope of the invention. The invention, therefore, should not be limited, except by the following claims, and their equivalents.

What is claimed is:

1. A method for simultaneous delivery of a therapeutically active amount of a powder formulation to both the lungs and the gastrointestinal tract of a patient comprising the steps of:

preparing a formulation of a pharmaceutical powder comprising active carrier particles and active microfine particles;

loading the formulation into a dry powder inhaler;

inhaling the formulation, with a therapeutically effective amount of the carrier particles passing into the patient's gastrointestinal tract.

2. The method of claim 1 wherein the formulation is substantially free of any excipient.

3. The method of claim 1 wherein the formulation comprises a pure single pharmaceutical compound.

4. The method of claim 1 wherein the microfine particles and the carrier particles are different pharmaceutical compounds.

5. The method of claim 1 wherein the microfine particles comprise at least one pharmaceutical compound, and the carrier particles comprise at least one pharmaceutical compound.

6. The method of claim 1 wherein the carrier particles have an average volume median diameter of 20–2000 microns and the microfine particles have an average volume median diameter of 1–10 microns.

7. The method of claim 1 wherein the inhaled microfine particles in the lung provide a fast acting therapeutic effect, and the carrier particles in the gastrointestinal tract provide a delayed onset of action therapeutic effect.

8. The method of claim 1 wherein the formulation comprises inactive excipient particles.

9. The method of claim 8 wherein the inactive excipient particles have an average volume median diameter of 1–250 microns.

10. The method of claim 1 wherein the dose delivered to the GI tract is 10–1,000 times greater than the dose delivered to the lungs.

11. The method of claim 7 wherein the particles in the lung provide a therapeutic effect within 15 minutes after inhalation and the particles in the GI tract provide a therapeutic effect which lasts for more than 30 minutes.

12. The method of claim 1 wherein the formulation has more particles in the size distribution of 1–10 microns average volume median diameter and in the size distribution of 30–300 microns average volume median diameter than in the size distribution range between 10 and 30 microns.

13. The method of claim 1 wherein the formulation has more particles in the size distribution of 1–10 microns average volume median diameter and in the size distribution of 50–100 microns average volume median diameter than in the size distribution range between 10 and 50 microns.

14. The method of claim 1 wherein the formulation has more particles in the size distribution of 1–5 microns average volume median diameter and in the size distribution of 30–300 microns average volume median diameter than the size distribution range between 5 and 30 microns.

15. The method of claim 1 wherein the formulation has more particles in the size distribution of 1–5 microns average volume median diameter and in the size distribution of 50–100 microns average volume median diameter than in the size distribution range between 5 and 50 microns.

16. The method of claim 1 further including the step of coating the carrier particles to provide a sustained therapeutic effect.

17. The method of claim 1 wherein the weight ratio of carrier particles to microfine particles ranges from 10/1 to 1000/1.

18. The method of claim 1 wherein the microfine particles comprise insulin and the carrier particles comprise an oral hypoglycemic or mimetics.

19. The method of claim 1 wherein the weight of the microfine particles does not exceed 50 mg.

20. The method of claim 1 wherein the carrier particles have an average diameter of from 20–2000 microns average volume median diameter.

21. The method of claim 1 wherein the carrier particles have a size ranging from 30–300 microns average volume median diameter.

22. The method of claim 1 wherein the carrier particles have a size ranging from 50–100 microns average volume median diameter.

23. A method for simultaneous delivery of a pharmaceutical formulation to both the lungs and the gastrointestinal tract, comprising the steps of:
   preparing a formulation of a substantially pure dry pharmaceutical powder including active inhalable particles having a diameter of 1–10 microns average volume median diameter and including carrier particles having at least 30 microns average volume median diameter, and with the carrier particles comprising the same pharmaceutical compound as the active particles;
   loading the formulation into a dry powder inhaler; and
   inhaling the formulation.

* * * * *